United States Patent [19]
Tatee et al.

[11] Patent Number: 5,610,315
[45] Date of Patent: Mar. 11, 1997

[54] PROCESS FOR THE PREPARATION OF 6,7-DIACYL-7-DEACETYLFORSKOLIN DERIVATIVES

[75] Inventors: Tochiro Tatee, Tokyo; Akira Shiozawa, Omiya; Hirotaka Yamamoto, Yono; Yuh-ichiro Ichikawa, Tokyo; Aya Ishikawa, Tokyo; Chikara Komuro, Tokyo; Kazuhisa Narita, Tokyo, all of Japan

[73] Assignee: Nippon Kayaku Kabushiki Kaisha, Tokyo, Japan

[21] Appl. No.: 442,403

[22] Filed: May 16, 1995

Related U.S. Application Data

[62] Division of Ser. No. 179,826, Jan. 19, 1994, Pat. No. 5,484,954, which is a division of Ser. No. 71,616, Jun. 4, 1993, Pat. No. 5,302,730, which is a continuation of Ser. No. 624,528, Dec. 10, 1990, abandoned, which is a continuation-in-part of Ser. No. 212,013, Jun. 27, 1988, abandoned.

[30] Foreign Application Priority Data

Jun. 29, 1987 [JP] Japan .................. 62-159638
Jun. 29, 1987 [JP] Japan .................. 62-159639

[51] Int. Cl.[6] ........................... C07D 311/92
[52] U.S. Cl. ............................. 549/389
[58] Field of Search ............................. 549/389

[56] References Cited

U.S. PATENT DOCUMENTS

| | | | |
|---|---|---|---|
| 4,088,659 | 5/1978 | Bhat et al. | |
| 4,134,986 | 1/1979 | Bajwa et al. | |
| 4,639,443 | 1/1987 | Kosley, Jr. et al. | 514/222 |
| 4,639,446 | 1/1987 | Kosley, Jr. et al. | 514/222 |

FOREIGN PATENT DOCUMENTS

| | | |
|---|---|---|
| 0116713 | 8/1984 | European Pat. Off. |
| 0191166 | 8/1986 | European Pat. Off. |
| 0193132 | 9/1986 | European Pat. Off. |
| 222413 | 5/1987 | European Pat. Off. |
| WO85/03637 | 8/1985 | WIPO |

OTHER PUBLICATIONS

Sujata V. Bhat, *Journal of the Chemical Society*, Perkins Transactions I, pp. 767–771 (Mar. 1982).

Bhat, "The Antihypertensive and Positive Inotropic Diterpene Forskolin: Effects of Structural Modifications on its Activity, *Journal of Medical Chemistry*," 26:486–492 (1983).

Metzger et al., "The Positive Inotropic–Acting Forskolin, a Potent Adenylatecyclase Activator", *Arzneimittel–Forschung*, 31:1248–1250 (1981).

Bhat, Jes, Perkins Transactions I, pp. 767–771 (1982).

*Primary Examiner*—Nicky Chan
*Attorney, Agent, or Firm*—Banner & Witcoff, Ltd.

[57] ABSTRACT

This invention relates to a process for the preparation of a 6,7-diacyl-7-deacetylforskolin derivative represented by the general formula:

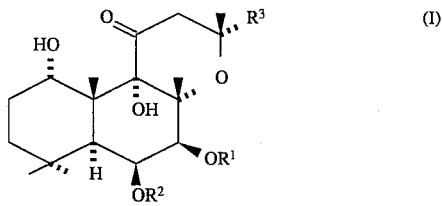

(I)

wherein $R^1$ and $R^2$ each stands for an acyl group and $R^3$ stands for an aliphatic group having 2 to 3 carbon atoms, which comprises eliminating the acyl group at position 1 in a 1,6,7-triacyl-7-deacetylforskolin derivative represented by the general formula:

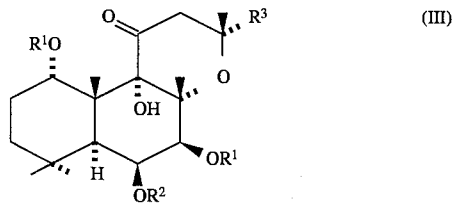

(III)

wherein $R^1$, $R^2$ and $R^3$ are as defined above, by solvolysis. The compound of the formula (I) is expected as medicine.

1 Claim, No Drawings

PROCESS FOR THE PREPARATION OF 6,7-DIACYL-7-DEACETYLFORSKOLIN DERIVATIVES

This application is a division of application Ser. No. 08/179,826, filed Jan. 19, 1994, now U.S. Pat. No. 5,484,954 which is a division of Ser. No. 08/071,616, filed Jun. 4, 1993, which is a continuation of Ser. No. 07/624,528, filed Dec. 10, 1990, now abandoned, which is a continuation-in-part of Ser. No. 07/212,013, filed Jun. 27, 1988, now abandoned.

BACKGROUND OF THE INVENTION

1. Field of the Invention

The present invention relates to a novel process for the preparation of a 6,7-diacyl-7-deacetylforskolin derivative which is expected as a medicine.

2. Description of the Prior Art

Known processes for the preparation of a 6,7-diacyl-7-deacetylforskolin derivative include a process which comprises directly acylating the hydroxyl group at position 7 of the compound of the general formula (II) (EP222413A).

However, the direct acylation process according to the prior art is disadvantageous in that the selectivity for the acetylation of the hydroxyl group at position 7 against position 1 is low.

SUMMARY OF THE INVENTION

The inventors of the present invention have eagerly studied and have found that high-quality 6,7-diacyl-7-deacetylforskolin derivative represented by the general formula:

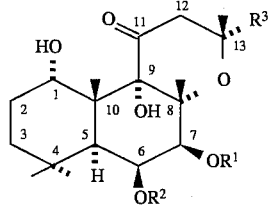

wherein $R^1$ and $R^2$ each stands for an acyl group and $R^3$ stands for an aliphatic group having 2 to 3 carbon atoms, or a cyclopropyl group can be unexpectedly prepared by acylating the hydroxy groups at positions 1 and 7 of a 6-acyl-7-deacetylforskolin derivative represented by the general formula:

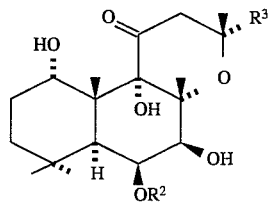

wherein $R^2$ and $R^3$ are as defined above, with an acylating agent to obtain a 1,6,7-triacyl-7-deacetylforskolin derivative represented by the general formula:

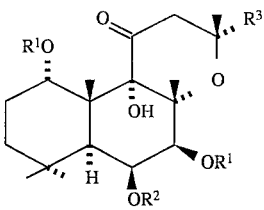

wherein $R^1$, $R^2$ and $R^3$ are as defined above, and subjecting the 1,6,7-triacyl-7-deacetylforskolin derivative to solvolysis to thereby selectively remove the acyl group at position i of the derivative.

The present invention has been accomplished on the basis of this finding.

DETAILED DESCRIPTION OF THE INVENTION

Examples of the acyl group of the $R^1$ in the general formulas (I) and (III) include formyl, acetyl, propionyl, butyryl, pentanoyl, hexanoyl, glycyl, dimethylaminoacetyl, piperidinoacetyl, t-butoxycarbonylaminoacetyl, glycoloyl, 2-morpholinopropionyl, 2-aminopropionyl, 3-dimethylaminopropionyl, 3-benzyloxycarbonylaminopropionyl, 2,3-dihydroxypropionyl, 2-pyrrolidinobutyryl, 3-thiomorpholinobutyryl, 4-dimethylaminobutyryl, 5-methylaminopentanoyl, 6-dimethylaminohexanoyl, tyrosyl, hemisuccinyl, thienoyl, prolyl, histidyl, lysyl, ornithyl, 2-dimethylaminopropionyl, 3-dimethylamino-2-methylpropionyl and 4-dimethylamino-2-methylbutyryl groups.

Examples of the acyl group of the $R^2$ in the general formulas (I), (II) and (III) include formyl, acetyl, propionyl, butyryl, pentanoyl, hexanoyl, glycyl, dimethylaminoacetyl, piperidinoacetyl, t-butoxycarbonylaminoacetyl, glycoloyl, 2-morpholinopropionyl, 2-aminopropionyl, 3-dimethylaminopropionyl, 3-benzyloxycarbonylaminopropionyl, 2,3-dihydroxypropionyl, 2-pyrrolidinobutyryl, 3-thiomorpholinobutyryl, 4-dimethylaminobutyryl, 5-methylaminopentanoyl, 6-dimethylaminohexanoyl, hemisuccinyl, thienoyl, prolyl, histidyl, lysyl, tyrosyl, ornithyl, 2-dimethylaminopropionyl, 3-dimethylamino-2-methylpropionyl, 4-dimethylamino-2-methylbutyryl and 2,2-dimethyl-1,3-dioxolane-4-carbonyl groups.

Examples of $R^3$ include aliphatic groups having 2 to 3 carbon atoms, such as vinyl and ethyl or cyclopropyl groups.

Examples of the compound of the general formula (II) include 7-deacetyl-6-dimethylaminoacetylforskolin, 7-deacetyl-6-glycylforskolin, 7-deacetyl-6-piperidinoacetylforskolin, 7-deacetyl-6-(2-dimethylaminopropionyl)forskolin, 7-deacetyl-6-(3-dimethylaminopropionyl)forskolin, 7-deacetyl-6-(2-morpholinopropionyl)forskolin, 7-deacetyl-6-alanylforskolin, 7-deacetyl-6-(2-aminobutyryl)forskolin, 7-deacetyl-6-(4-dimethylaminobutyryl)forskolin, 7-deacetyl-6-(2,3-dihydroxypropionyl)forskolin, 7-deacetyl-6-hemisuccinylforskolin, 7-deacetyl-6-histidylforskolin, 7-deacetyl-6-prolylforskolin, 7-deacetyl-6-lysylforskolin, 7-deacetyl-6-glycoloylforskolin, 7-deacetyl-14,15-dihydro-6-dimethylaminoacetylforskolin, 7-deacetyl-14,15-dihydro-6-(3-dimethylaminopropionyl)forskolin, 7-deacetyl-14,15-dihydro-6-(4-dimethylaminobutyryl)forskolin, 13-cyclopropyl-7-deacetyl-6-(3-dimethylaminopropionyl)-14,15-dinorforskolin, 13-cyclopropyl-7-deacetyl-6-(4-dimethylaminobutyryl)-14,15-dinorforskolin, 7-deacetyl-14,15-dihydro-6-piperidinoacetylforskolin, 7-deacetyl-14,15-dihydro-6-(2-morpholinopropionyl)forskolin, 7-deacetyl-6-(t-butoxycarbonylaminoacetyl)forskolin, 7-deacetyl-6-(2-benzyloxycarbonylaminopropionyl)forskolin, 7-deacetyl-6-(2-t-butoxycarbonylaminobutyryl)forskolin, 7-deacetylforskolin-6-(2,2-dimethyl-1,3-dioxolane-4-carboxylate), 7-deacetyl-6-(3-methoxycarbonylpropionyl)forskolin, 7-deacetyl-6-(3-dimethylamino-2-methylpropionyl)forskolin, 7-deacetyl-14,15-dihydro-6-(3-dimethylamino-2-methylpropionyl)forskolin, 7-deacetyl-6-(4-dimethylamino-2-methylbutyryl)forskolin, 7-deacetyl-14,15-dihydro-6-(4-dimethylamino-2-methylbutyryl)forskolin, 13-cyclopropyl-7-deacetyl-6-(3-dimethylamino-2-methylpropionyl)-14,15-dinorforskolin and 13-cyclopropyl-7-deacetyl-6-(4-dimethylamino-2-methylbutyryl)-14,15-dinorforskolin.

Examples of the compound represented by the general formula (III) include 1-formyl-6-dimethylaminoacetyl-7-deacetyl-7-formylforskolin, 1-acetyl-6-dimethylaminoacetylforskolin, 1-propionyl-6-dimethylaminoacetyl-7-deacetyl-7-propionylforskolin, 1-acetyl-6-piperidinoacetylforskolin, 1-butyryl-6-piperidinoacetyl-7-deacetyl-7-butyrylforskolin, 1-acetyl-6-(2-dimethylaminopropionyl)forskolin, 1-pentanoyl-6-(2-dimethylaminopropionyl)-7-deacetyl-7-pentanoylforskolin, 1-acetyl-6-(3-dimethylaminopropionyl)forskolin, 1-hexanoyl-6-(3-dimethylaminopropionyl)-7-deacetyl-7-hexanoylforskolin, 1-dimethylaminoacetyl-6-(3-dimethylaminopropionyl)-7-deacetyl-7-dimethylaminoacetylforskolin, 1-piperidinoacetyl-6-(3-dimethylaminopropionyl)-7-deacetyl-7-piperidinoacetylforskolin, 1-(t-butoxycarbonylaminoacetyl)-6-(3-dimethylaminopropionyl)-7-deacetyl-7-(t-butoxycarbonylaminoacetyl)forskolin, 1-acetyl-6-(2-morpholinopropionyl)forskolin, 1-(2-morpholinopropionyl)-6-(2-morpholinopropionyl)-7-deacetyl-7-(2-morpholinopropionyl)forskolin, 1-acetyl-6-(4-dimethylaminobutyryl)forskolin, 1-(3-dimethylaminopropionyl)-6-(4-dimethylaminobutyryl)-7-deacetyl-7-(3-dimethylaminopropionyl)forskolin, 1-(3-benzyloxycarbonylaminopropionyl)-6-(4-dimethylaminobutyryl)-7-deacetyl-7-(3-benzyloxycarbonylaminopropionyl)forskolin, 1-(2-pyrrolidinobutyryl)-6-(4-dimethylaminobutyryl)-7-deacetyl-7-(2-pyrrolidinobutyryl)forskolin, 1-acetyl-6-hemisuccinylforskolin, 1-(3-thiomorpholinobutyryl)-6-hemisuccinyl-7-deacetyl-7-(3-thiomorpholinobutyryl)forskolin, 1-acetyl-14,15-dihydro-6-dimethylaminoacetylforskolin, 1-(4-dimethylaminobutyryl)-14,15-dihydro-6-dimethylaminoacetyl-7-deacetyl-7-(4-dimethylaminobutyryl)forskolin, 1-acetyl-14,15-dihydro-6-(3-dimethylaminopropionyl)forskolin, 1-(6-dimethylaminohexanoyl)-14,15-dihydro-6-(3-dimethylaminopropionyl)-7-deacetyl-7-(6-dimethylaminohexanoyl)forskolin, 1-acetyl-14,15-dihydro-6-(4-dimethylaminobutyryl)forskolin, 1-propionyl-14,15-dihydro-6-(4-dimethylaminobutyryl)-7-deacetyl-7-propionylforskolin, 1-acetyl-13-cyclopropyl-6-(3-dimethylaminopropionyl)-14,15-dinorforskolin, 1-acetyl-13-cyclopropyl-6-(4-dimethylaminobutyryl)-14,15-dinorforskolin, 1-acetyl-14,15-dihydro-6-piperidinoacetylforskolin, 1-acetyl-14,15-dihydro-6-(2-morpholinopropionyl)forskolin, 1-acetyl-6-(3-dimethylamino-2-methylpropionyl)forskolin, 1-acetyl-14,15-dihydro-6-(3-dimethylamino-2-methylpropionyl)forskolin, 1-acetyl-13-cyclopropyl-6-(3-dimethylamino-2-methylpropionyl)-14,15-dinorforskolin, 1-acetyl-6-(4-dimethylamino-2-methylbutyryl)forskolin, 1-acetyl-14,15-dihydro-6-(4-dimethylamino-2-methylbutyryl)forskolin and 1-acetyl-13-cyclopropyl-6-(4-dimethylamino-2-methylbutyryl)-14,15-dinorforskolin.

Examples of the acylating agent to be used in the present invention include formic acid, acetic acid, propionic acid, butyric acid, valeric acid, caproic acid, glycine, N,N-dimethylglycine, piperidinoacetic acid, N-t-butoxycarbonylglycine, glycolic acid, 2-morpholinopropionic acid, alanine, 3-dimethylaminopropionic acid, 3-benzyloxycarbonylaminopropionic acid, 2,3-dihydroxypropionic acid, 2-pyrrolidinobutyric acid, 3-thiomorpholinobutyric acid, 4-dimethylaminobutyric acid, 5-methylaminovaleic acid, 6-dimethylaminocaproic acid, tyrosine, succinic acid, proline, histidine, lysine, ornithine, thiophenecarboxylic acid, 2,2-dimethyl-1,3-dioxolane-4-carboxylic acid, 3-dimethylamino-2-methylpropionic acid, 4-dimethylamino-2-methylbutyric acid and reactive derivatives thereof.

Such a reactive derivative includes acid halides, acid anhydrides, mixed acid anhydrides and Leuch's anhydrides.

The acylation of the compound of the general formula (II) is carried out by the use of about 2 to about 50 mol, preferably about 2 to about 4 mol of an acylating agent per mol of the compound in a solvent at a temperature of about 0° C. to a boiling point of the solvent, preferably about 0° C. to room temperature for several minutes to about 24 hours, preferably several minutes to about 2 hours. Examples of the solvent to be used in the acylation include benzene, chloroform, ether, dichloromethane, 1,1,1-trichloroethane, 1,2-dichloroethane, carbon tetrachloride and ethyl acetate.

The selective deacylation at position 1 of the compound of the general formula (III) prepared by the above acylation at position 1 is carried out by any process selected from among alcoholysis, aminolysis and hydrolysis, preferably by hydrolysis. The hydrolysis is carried out in the presence of a hydrolyzing agent in a solvent at a temperature of about 0° C. to a boiling point of the solvent, preferably about 0° C. to room temperature for about one minute to about 12 hours, preferably about 5 minutes to about 3 hours. It is preferred that the reaction time be short, when the reaction temperature is high, while the time be long, when the temperature is low. Examples of the solvent to be used in the hydrolysis include water soluble solvent such as alcohol (methanol, ethanol, propanol, isopropanol, butanol, etc.), acetonitrile, dimethyl, sulfoxide, N,N-dimethylformamide, acetone, tetrahydrofuran and mixtures thereof with water up to 50 v/v %, preferably aqueous $C_1$–$C_4$ alcohol containing about 0.5 to about 20 v/v % of water. The hydrolyzing agent is a base or an acid.

The base to be used in the hydrolysis include alkali hydroxides such as sodium hydroxide and potassium hydroxide; alkali carbonates such as potassium carbonate; alkali bicarbonates such as sodium bicarbonate and amines such as ammonia and triethylamine, while the acid include mineral acids such as sulfuric and hydrochloric acids. Such a base or acid is contained in a solvent with a concentration of about 0.01 to about 50%, preferably about 0.05 to about 10 %.

When any of $R^1$ and $R^2$ is a propionyl group having an amino substituent at β-position, for example, a dimethylaminopropionyl group, it is preferred that the reaction mixture after the acylation or after the selective deacylation be treated with an amine corresponding to the amino substituent in a solvent at a temperature of 0° C. to room temperature for one minute to 12 hours to thereby inhibit the formation of a by-product. Examples of the solvent to be used in this treatment include benzene, carbon tetrachloride, dichloromethane, chloroform, 1,2-dichloroethane, 1,1,1-trichloroethane, ether, diisopropyl ether, ethyl acetate, acetone, propanol, ethanol and methanol.

Further, the above amine may be used in an amount of about 0.1 to about 3 mol per mole of the compound of the general formula (II) used.

If circumstances requires, excesses of selective deacetylation arises to obtain compound (II). But the excesses of the reaction can be avoided by neutrelization after the completion of selective deacetylation.

After the completion of the reaction, a 6,7-diacyl-7-deacetylforskolin derivative thus prepared can be isolated by concentrating the reaction mixture, optionally diluting the obtained residue with water or an aqueous solution of common salt, extracting the obtained mixture with an organic solvent, washing the organic layer, drying and concentrating the washed layer and recrystallizing the obtained residue. Thus, according to the present invention, the desired compound can be easily purified without employing chromatography or the like.

The yields of the objective compounds prepared by the process of the present invention (Example 1-1 or 1-2) and by the process described in E.P. 222413A are shown in Table 1.

TABLE 1

| | Yield | |
|---|---|---|
| | 6-(4-dimethylamino-butyryl)-forskolin [yield based on 7-deacetyl-6-(4-dimethyl-aminobutyryl) forskolin] | 6-(3-dimethylamino-propionyl)-forskolin [yield based on 7-deacetyl-6-(3-dimethyl-aminopropionyl) forskolin] |
| The process of the present invention | 83% (Ex. 1-1) | 54% (Ex. 1-2) |
| The process of the prior art | 31% | 32% |

It is apparent from the results shown in the above table that a 6,7-diacyl-7-deacetylforskolin can be prepared by the process of the present invention in a high yield.

The process described in E.P. 222413A mentioned above is as follows:

A solution of 6-acyl-7-deacetylforskolin in dichloromethane is reacted with acetyl chloride in the presence of pyridine. After the completion of the reaction, the reaction product is purified by silica gel chromatography.

EXAMPLE 1-1

6-(4-Dimethylaminobutyryl)forskolin 30 ml of acetic anhydride was added to a mixture comprising 31.7 g of 7-deacetyl-6-(4-dimethylaminobutyryl)forskolin, 0.5 g of 4-dimethylaminopyridine and 120 ml of pyridine under cooling with ice. The mixture was stirred at room temperature for two days. After the completion of the reaction, the reaction mixture was concentrated.

The concentrate was dissolved in 600 ml of methanol, followed by the addition of 250 ml of 1N aqueous sodium hydroxide. The mixture was stirred at a room temperature for 35 minutes and filtered to give 31.2 g of a crude crystal. This crude crystal was recrystallized from acetone to give 28.7 g of 6-(4-dimethylaminobutyryl)forskolin [yield based on 7-deacetyl-6-(4-dimethylaminobutyryl)forskolin: 83%].

IR(KBr)ν: 3450, 1730, 1710 cm$^{-1}$.

The reaction product before the hydrolysis in the above synthesis was purified by silica gel column chromatography to obtain 1-acetyl-6-(4-dimethylaminobutyryl)forskolin.

$^1$H-NMR (CDCl$_3$)δ: 5.84 (1H, t, J=3.5 Hz), 5.57 (1H, brs), 5.56 (1H, d, J=4.8 Hz), 2.41 (6H, s), 2.03 (6H, s), 1.64 (3H, s), 1.52 (3H, s), 1.34 (3H, s), 1.04 (3H, s), 0.97 (3H, s).

EXAMPLE 1-2

6-(3-Dimethylaminopropionyl)forskolin

A mixture comprising 12 g of 7-deacetyl-6-(3-dimethylaminopropionyl)forskolin, 35 mg of 4-dimethylaminopyridine, 48 ml of anhydrous pyridine and 5.9 ml of acetic anhydride was stirred at room temperature for 2 hours, followed by the addition of 35 mg of 4-dimethylaminopyridine. The mixture was further stirred for 3 hours. After the completion of the reaction, 5 ml of methanol was added to the reaction mixture and the mixture was concentrated.

The concentrate was diluted with 120 ml of methanol and 25 ml of water, followed by the addition of 40 ml of 1N aqueous sodium hydroxide. The mixture was stirred at room temperature for 30 minutes. 50 ml of 1N hydrochloric acid was added to the mixture to stop the reaction and the mixture was concentrated. The concentrate was diluted with water, basified with concentrated aqueous ammonia and extracted with diisopropyl ether. The organic layer was dried over anhydrous magnesium sulfate and filtered to remove the drying agent. The filtrate was concentrated to give 13.4 g of a residue. This residue was dissolved in dichloromethane, followed by the addition of dimethylamine. The mixture was stirred at a room temperature for one hour. After the completion of the reaction, the reaction mixture was concentrated to give a residue. This residue was recrystallized from ethanol and then from cyclohexane/dichloromethane to give 7.04 g of 6-(3-dimethylaminopropionyl)forskolin [yield based on 7-deacetyl-6-(3-dimethylaminopropionyl)forskolin: 54%].

IR(KBr)ν: 3200, 1735, 1710 cm$^{-1}$.

The reaction product obtained before the hydrolysis in the above synthesis of 6-(3-dimethylaminopropionyl)forskolin was purified by silica gel column chromatography to give 1-acetyl-6-(3-dimethylaminopropionyl)forskolin.

IR(Nujol)ν: 3500, 1735, 1710 cm$^{-1}$.

$^1$H-NMR (CDCl$_3$)δ: 5.85 (1H, q, J=4.8 Hz, J=2.9 Hz), 5.57 (1H, brs), 5.55 (1H, d, J=4.8 Hz), 2.32 (6H, s), 2.023 (3H, s), 2.020 (3H, s), 1.65 (3H, s), 1.53 (3H, s), 1.34 (3H, s), 1.04 (3H, s), 0.98 (3H, s).

MS (hydrochloride) m/z (relative intensity): 552 (M$^+$ of free base, 18), 160 (22), 118 (70), 116 (33), 59 (39), 58 (100).

EXAMPLE 1-3

1-Acetyl-6-(2-morpholinopropionyl)forskolin

A solution of 945 mg of acetyl chloride in dichloromethane was added in six portions to a mixture comprising 700 mg of 7-deacetyl-6-(2-morpholinopropionyl)froskolin, 1 g of pyridine and 30 ml of dichloromethane at room temperature over a period of 9 hours. After the completion of the reaction, water was added to the reaction mixture and the mixture was basified with 20% aqueous sodium hydroxide and extracted with dichloromethane. The organic layer was dried over anhydrous magnesium sulfate and filtered to remove the drying agent. The filtrate was concentrated to give a residue. This residue was recrystallized from hexane/toluene to obtain 606 mg of 1-acetyl-6-(2-morpholinopropionyl)forskolin as a colorless solid diastereomeric mixture (yield: 75%).

IR(Nujol)ν: 3490, 1750, 1715, 1230 cm$^{-1}$.

MS m/z (relative intensity): 593 (M$^+$, 0.03), 549 (0.7), 518 (0.5), 410 (0.7), 228 (0.9), 191 (1.2), 160 (8), 115 (23), 114 (100), 70 (9).

6-(2-Morpholinopropionyl)forskolin 0.75 ml of 1N aqueous sodium hydroxide was added to a mixture comprising 372 mg of 1-acetyl-6-(2-morpholinopropionyl)forskolin and 20 ml of methanol. The mixture was stirred at room temperature for 30 minutes. After the completion of the reaction, the reaction mixture was concentrated. The concentrate was diluted with a saturated aqueous solution of common salt and extracted with ethyl acetate. The organic layer was dried over anhydrous magnesium sulfate and filtered to remove the drying agent. The filtrate was concentrated to give 388 mg of a solid residue. This residue was recrystallized from hexane/ethyl acetate to give 214 mg of 6-(2-morpholinopropionyl)forskolin (yield: 62%).

IR(Nujol)ν: 3170, 1735, 1710 cm$^{-1}$.

MS m/z (relative intensity): 551 (M$^+$, 0.2), 518 (2), 158 (20), 115 (100), 114 (100), 70 (47).

EXAMPLE 1-4

6-Piperidinoacetylforskolin 520 mg of acetic anhydride was added to a mixture comprising 188 mg of 7-deacetyl-6-piperidinoacetylforskolin, 10 mg of 4-dimethylaminopyridine and 4 ml of pyridine under cooling with ice. The mixture was stirred at a room temperature for 3.5 hours. After the completion of the reaction, methanol was added to the reaction mixture under cooling with ice. The mixture was concentrated to give an oily residue. A saturated aqueous solution of common salt was added to the residue. The obtained mixture was basified with concentrated aqueous ammonia and extracted with ethyl acetate. The organic layer was dried over anhydrous magnesium sulfate and filtered to remove the drying agent. The filtrate was concentrated to give 224 mg of a solid product. 120 mg of this product was dissolved in 5 ml of methanol, followed by the addition of 0.20 ml of 1N aqueous sodium hydroxide. The mixture was stirred at a room temperature for 25 minutes. After the completion of the reaction, the reaction mixture was concentrated. The concentrate was diluted with a saturated aqueous solution of common salt and extracted with ethyl acetate. The organic layer was dried over anhydrous magnesium sulfate and filtered to remove the drying agent. The filtrate was concentrated to obtain 113 mg of a residue. This residue was recrylstallized from hexane/ethyl acetate to obtain 59 mg of 6-piperidinoacetylforskolin [yield based on 7-deacetyl-6-piperidinoacetylforskolin: 54%].

IR(Nujol)ν: 3180, 1745, 1710 cm$^{-1}$ $^1$H-NMR (CDCl$_3$)δ: 5.85 (1H, q, J=4.2 Hz, J=2.7 Hz), 5.55 (1H, d, J=4.4 Hz), 4.61 (1H, br, s), 3.18 and 3.14 (each 1H, d, J=16 Hz), 2.5 (4H, m), 2.03 (3H, s), 1.66 (3H, s), 1.44 (3H, s), 1.35 (3H, s), 1.03 (3H, s), 0.96 (3H, s)

MS m/z: 535 (M$^+$)

The reaction product before the selective hydrolysis with sodium hydroxide in the above synthesis was purified by silica gel column chromatography to give 1-acetyl-6-piperidinoacetylforskolin.

MS m/z: 577 (M$^+$)

EXAMPLE 1-5

6-(3-Dimethylaminopropionyl)-14,15-dihydroforskolin hydrochloride

A mixture comprising 200 mg of 7-deacetyl-6-(3-dimethylaminopropionyl)-14,15-dihydroforskolin, 7 mg of 4-dimethylaminopyridine, 2 ml of anhydrous pyridine and 0.4 ml of acetic anhydride was stirred at a room temperature for 3 hours. After the completion of the reaction, 1 ml of methanol was added to the reaction mixture under cooling with ice and the mixture was concentrated.

The concentrate was diluted with a saturated aqueous solution of common salt, basified with concentrated aqueous ammonia, and extracted with ethyl acetate. The organic layer was dried over anhydrous magnesium sulfate and filtered to remove the drying agent. The filtrate was concentrated to obtain 1-acetyl-6-(3-dimethylaminopropionyl)-14,15-dihydroforskolin (231 mg).

The concentrate was diluted with 2 ml of methanol, followed by the addition of 0.4 ml of 0.25N aqueous sodium hydroxide under cooling with ice. The mixture was stirred under cooling with ice for 1.5 hours. 0.6 ml of 1N hydrochloric acid was added to the mixture to stop the reaction and the mixture was concentrated. The concentrate was diluted with water, basified with concentrated aqueous ammonia and extracted with ethyl acetate. The organic layer was dried over anhydrous magnesium sulfate and filtered to remove the drying agent. The filtrate was concentrated to give 202 mg of a residue. This residue was dissolved in 2 ml of dichloromethane, followed by the addition of 0.15 ml of 4N hydrochloric acid in dioxane. The mixture was concentrated to give 210 mg of a solid residue. This residue was recrystallized from methanol-ethyl acetate (2:3) to give 112 mg of 6-(3-dimethylaminopropionyl)-14,15-dihydroforskolin hydrochloride [yield based on 7-deacetyl-6-(3-dimethylaminopropionyl)-14,15-dihydroforskolin: 48%].

Reference Example 1

7-Deacetyl-6-(3-dimethylaminopropionyl)-14,15-dihydroforskolin

A mixture of 703 mg of 7-deacetyl-6-(3-dimethylaminopropionyl)forskolin, 23 mg of 5% palladium on carbon catalyst, and 20 ml of methanol was stirred under a hydrogen atmosphere at room temperature for 1 hour and 40 minutes to complete the reaction. The reaction mixture was filtered to remove the catalyst. The filtrate was concentrated to obtain 689 mg of a solid residue. This residue was recrystallized from chloroform-isopropyl ether (1:5) to obtain 541 mg of 7-deacetyl-6-(3-dimethylaminopropionyl)-14,15-dihydroforskolin (yield: 77%).

m.p. 163°–165° C.

IR(Nujol)ν: 3200, 1735, 1705 cm$^{-1}$ $^1$H-NMR (CDCl$_3$)δ: 5.94 (1H, t, J=4 Hz), 4.50 (1H, brs), 4.18 (1H, d, J=5 Hz), 2.26 (6H, s), 1.53 (3H, s), 1.42 (3H, s), 1.31 (3H, s), 1.10 (3H, s), 0.97 (3H, t, J=7 Hz), 0.95 (3H, s).

MS m/z (relative intensity): 469 (M$^+$, 5), 159 (13), 118 (48), 116 (12), 91 (30), 69 (13), 59 (10), 58 (100), 57 (11), 55 (13).

The second invention of the present invention relates to a novel process for the preparation of a 6-acyl-7-deacetylforskolin derivative which is noted as a medicine, or starting material of the first invention.

Known processes for the preparation of a 6-acyl-7-deacetylforskolin include a process comprising treating 7-acyl-7-deacetylforskolin with an alkali in a solvent at room temperature to thereby carry out the rearrangement of the acyl group at position 7 to position 6 (see E.P. No. 222413A).

In the above process of the prior art, 7-deacetylforskolin is formed by the hydrolysis of 7-acyl-7-deacetylforskolin as a by-product. Therefore, the process is problematic in yield and is disadvantageous in that a product obtained by the process must be purified by chromatography, thus being unsuitable for large scale production.

The inventors of the present invention have eagerly investigated and have found that a 6-acyl-7-deacetylforskolin derivative represented by the general formula:

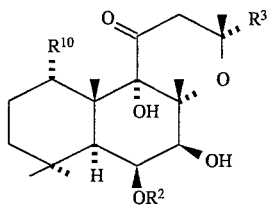

wherein $R^{10}$ stands for a hydroxy group which may be esterified; $R^2$ stands for an acyl group and $R^3$ stands for an aliphatic group having 2 to 3 carbon atoms, or a cyclopropyl group can be prepared, without using any alkali, only by heating a 7-acyl-7-deacetylforskolin derivative represented by the general formula:

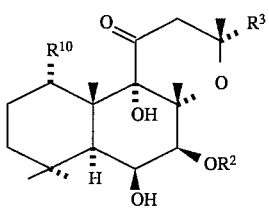

wherein $R^{10}$, $R^2$ and $R^3$ are as defined above to thereby carry out the rearrangement of the acyl group at position 7 to position 6.

The $R^{10}$ of the above general formulas (1) and (2) includes a hydroxy group; acyloxy groups such as formyloxy, acetoxy, propionyloxy, butyryloxy, benzoyloxy, 4-methoxybenzoyloxy, dimethylaminoacetoxy, piperidinoacetoxy, diethylaminoacetoxy, morpholinoacetoxy, (4-hydroxypiperidino)acetoxy, dipropylaminoacetoxy, 2-ethylaminopropionyloxy, thiomorpholinoacetoxy, 2-morpholinopropionyloxy, isopropylaminoacetoxy, 2-dimethylaminopropionyloxy, t-butylaminoacetoxy, 3-dimethylaminopropionyloxy, (4-methylpiperazino)acetoxy, 2-dimethylaminobutyryloxy, 3-dimethylaminobutyryloxy, 4-dimethylaminobutyryloxy, glycoloyloxy, 2,3-dihydroxypropionyloxy, thioglycoloyloxy, hemisuccinyloxy, hemiglutaryloxy, glycyloxy, 2-aminopropionyloxy, 3-aminopropionyloxy, 2-methylaminobutyryloxy, nicotinoyloxy, furoyloxy, histidyloxy and lysyloxy; silyloxy groups such as trimethylsilyloxy, t-butyldiphenylsilyloxy and t-butyldimethylsilyloxy groups; substituted alkoxy groups such as 2-methoxyethoxymethoxy, methoxy, methylthiomethoxy, methoxymethoxy and benzyloxy groups and substituted alkoxycarbonyloxy groups such as benzyloxycarbonyloxy and t-butoxycarbonyloxy groups.

The $R^2$ includes formyl, acetyl, propionyl, butyryl, dimethylaminoacetyl, butylaminoacetyl, diethylaminoacetyl, pyrrolidinoacetyl, piperazinoacetyl, morpholinoacetyl, piperidinoacetyl, N-cyclohexyl-N-methylaminoacetyl, (4-methylpiperazino)acetyl, dipropylaminoacetyl, (4-hydroxypiperidino)acetyl, thiomorpholinoacetyl, isopropylaminoacetyl, t-butylaminoacetyl, glycyl, benzyloxycarbonylaminoacetyl, 2-aminopropionyl, 3-aminopropionyl, 2-dimethylaminopropionyl, 3-dimethylaminopropionyl, 2-pyrrolidinopropionyl, 3-piperazinopropionyl, 2-butylaminopropionyl, 3-diethylaminopropionyl, 2-morpholinopropionyl, 3-piperidinopropionyl, 3-(t-butoxycarbonylamino)propionyl, 2-aminobutyryl, 3-aminobutyryl, 4-dimethylaminobutyryl, 4-aminobutyryl, 2-dimethylaminobutyryl, 3-diethylaminobutyryl, 4-isopropylaminobutyryl, 2-butylaminobutyryl, 3-pyrrolidinobutyryl, 4-morpholinobutyryl, 2-piperazinobutyryl, 3-piperidinobutyryl, 4-thimorpholinobutyryl, 2-aminopentanoyl, 3-dimethylaminopentanoyl, 4-diethylaminopentanoyl, 5-pyrrolidinopentanoyl, 2-piperidinohexanoyl, 3-morpholinohexanoyl, 4-(4-methylpiperazino)hexanoyl, 5-(6-butylamino)hexanoyl, 6-methylaminohexanoyl, 3-dimethylamino-2-methylpropionyl, 3-pyrrolidino-2-methylpropionyl, 3-dimethylamino-2-ethylpropionyl, 4-dimethylamino-2-methylbutyryl, 4-amino-2-propylbutyryl, hemisuccinyl, hemiglutaryl, thioglycoloyl, thienoyl, isonicotinoyl, prolyl, histidyl, lysyl, tyrosyl, methionyl, ornithyl, glycoloyl, lactoyl and 2,3-dihydroxypropionyl groups.

Examples of the $R^3$ group include aliphatic groups having 2 to 3 carbon atoms, such as vinyl and ethyl, or a cyclopropyl group.

Examples of the compound represented by the general formula (2) include 7-deacetyl-7-dimethylaminoacetylforskolin, 7-deacetyl-7-glycylforskolin, 7-deacetyl-7-piperidinoacetylforskolin, 7-deacetyl-7-(2-dimethylaminopropionyl)forskolin, 7-deacetyl-7-(3-dimethylaminopropionyl)forskolin, 7-deacetyl-7-(2-morpholinopropionyl)forskolin, 7-deacetyl-7-alanylforskolin, 7-deacetyl-7-(2-aminobutyryl)forskolin, 7-deacetyl-7-(4-dimethylaminobutyryl)forskolin, 7-deacetyl-7-(2,3-dihydroxypropionyl)forskolin, 7-deacetyl-7-hemisuccinylforskolin, 7-deacetyl-7-histidylforskolin, 7-deacetyl-7-propionylforskolin, 7-deacetyl-7-lysylforskolin, 7-deacetyl-7-glycoloylforskolin, 7-deacetyl-14,15-dihydro-7-dimethylaminoacetylforskolin, 7-deacetyl-14,15-dihydro-7-(3-dimethylaminopropionyl)forskolin, 7-deacetyl-14,15-dihydro-7-(4-dimethylaminobutyryl)forskolin, 13-cyclopropyl-7-deacetyl-7-(3-dimethylaminopropionyl)-14,15-dinorforskolin, 13-cyclopropyl-7-deacetyl-7-(4-dimethylaminobutyryl)-4,15-dinorforskolin, 7-deacetyl-14,15-dihydro-7-pyrrolidinoacetylforskolin, 7-deacetyl-14,15-dihydro-7-(2-morpholinopropionyl)forskolin, 1-acetylforskolin, 1-t-butyldimethylsilylforskolin, 1-benzoylforskolin, 1-benzylforskolin, 1-methylforskolin, 1-trimethylsilylforskolin, 1-t-butyldiphenylsilylforskolin, 1-(2-methoxyethoxymethyl)forskolin, 1-methylthiomethylforskolin, 1-methoxymethylforskolin, 1-benzyloxycarbonylforskolin, 1-(t-butoxycarbonyl)forskolin, 1-acetyl-7-deacetyl-7-propionylforskolin, 1-t-butyldimethylsilyl-7-butyryl-7-deacetylforskolin, 1-benzyl-7-deacetyl-7-pentanoylforskolin, 7-deacetyl-7-hexanoyl-1-(2-methoxyethoxymethyl)forskolin, 1-benzoyl-14,15-dihydroforskolin, 14,15-dihydro-1-trimethylsilylforskolin, 1-methoxy-14,15-dihydro-7-deacetyl-7-propionylforskolin, 1-t-butyldiphenylsilyl-13-cyclopropyl-14,15-dionor-7-deacetyl-7-butyrylforskolin, 1-benzyl-13-cyclopropyl-14,15-dinor-7-deacetyl-7-(3-dimethylaminopropionyl)forskolin, 1-(t-butoxycarbonyl)-13-cyclopropyl-14,15-dinor-7-deacetyl-7-(4-dimethylaminobutyryl)forskolin, 1-methylthiomethyl-13-cyclopropyl-14,15-dinor-7-deacetyl-7-dimethylaminoacetylforskolin, 14,15-dihydroforskolin, 13-cyclopropyl-14,15-dinorforskolin, 7-deacetylforskolin-7-(2,2-dimethyl-1,3-dioxolane-4-carbonyl), 7-deacetyl-7-(3-dimethylamino-2-methylpropionyl)forskolin, 14,15-dihydro-7-deacetyl-7-(3-dimethylamino-2-methylpropionyl)forskolin, 7-deacetyl-7-(4-dimethylamino-2-methylbutyryl)forskolin and 14,15-dihydro-7-deacetyl-7-(4-dimethylamino-2-methylbutyryl)forskolin.

According to the present invention, in case of using no solvent, the compound of the general formula (2) must be heated to at least 100° C., preferably 130° to 300° C., still preferably 150° to 250° C. In case of using solvent, reaction temperature is at least about 50° C., preferably about 70° C. to boiling point of the solvent.

Although the heating time varies depending upon the temperature, it is generally at least 1 minute, preferably 5 minutes to 10 hours, still preferably 15 to 60 minutes in case of using no solvent, and 3 to 8 hours in case of using solvent.

The method for heating the compound of the general formula (2) is not particularly limited and the heating of the compound may be carried out either directly or in a solvent. In the direct heating, the rearrangement is preferably carried out in a molten state. On the other hand, in the heating using a solvent, although the solvent may be either one in which the compound of the formula (2) is soluble or one in which the compound is insoluble, the solvent is preferably an anhydrous one in order to inhibit the deacylation of the compound caused by hydrolysis. Preferred examples of the anhydrous solvent include N,N-dimethylformamide, dimethyl sulfoxide, sulfolane, 1-methyl-2-pyrrolidinone, 1,1,2,2-tetrachloroethane, nitrobenzene, chlorobenzene, liquid paraffin, 1,1,2,2-tetrachloroethylene, octyl acetate, diglyme, triglyme, acetic acid, pyridine, acetonitrile, triethylamine, and butyronitrile o After the completion of the reaction, the reaction mixture is cooled to room temperature and recrystallized to obtain 6-acyl-7-deacetylforskolin.

When the $R^2$ is a propionyl group having an amino substituent at the β-position, for example, a 3-dimethylaminopropionyl group, it is preferred that the reaction mixture after the completion of the rearrangement is treated with an amine corresponding to the amino substituent at a temperature of 0° C. to room temperature for 1 minute to 12 hours to thereby inhibit the formation of a by-product. Examples of the solvent to be used in this treatment include benzene, carbon tetrachloride, dichloromethane, chloroform, 1,2-dichloroethane, 1,1,1-trichloroethane, ether, diisorpopyl ether, ethyl acetate, acetonitrile, butyronitrile, N,N-dimethylformamide, dimethylsulfoxide, sulfolane, 1-methyl-2-pyrrolidinone, pyridine and acetone. The amount of the amine to be used may be 0.1 to 3 mol per mol of the compound of the formula (2) used.

The yield (in terms of pure product) and purity of the objective compound obtained by the process according to the present invention (Example 2-1 or 2-4) or by the process of E.P. No. 222413A are shown in Table 2 together with the yield of a by-product (7-deacetylforskolin).

TABLE 2

| Starting material | | 7-Deacetyl-7-(4-dimethyl-aminobutyryl)forskolin | 7-Deacetyl-7-(3-dimethylamino-propionyl)forskolin |
|---|---|---|---|
| Ex. | desired compound | | |
| | yield | 84% (Ex. 2-1) | 74% (Ex. 2-4) |
| | purity* | 99.5% | 99.7% |
| | by-product | 0% | 0% |
| Comp. | desired compound | | |
| Ex. | yield | 36.9% | 52.2% |

TABLE 2-continued

| Starting material | 7-Deacetyl-7-(4-dimethyl-aminobutyryl)forskolin | 7-Deacetyl-7-(3-dimethylamino-propionyl)forskolin |
|---|---|---|
| purity* | 97% | 60% |
| by-product | 5% | 3% |

*determined by high-performance liquid chromatography

It is apparent from the results shown in the above table 2 that 6-acyl-7-deacetylforskolins of high purity can be prepared in a high yield by the process of the present invention without formation of a by-product.

The process of E.P. No. 222413A described above comprises treating 7-deacetyl-7-(4-dimethylaminobutyryl)forskolin or 7-deacetyl-7-(3-dimethylaminopropionyl)forskolin with sodium hydroxide in an acetonitrile/water (45:55) mixture.

EXAMPLE 2-1

7-Deacetyl-6-(4-dimethylaminobutyryl)forskolin 29.05 g of 7-deacetyl-7-(4-dimethylaminobutyryl)forskolin was heated to 160° C., stirred for 10 minutes in a molten state, and then, cooled to room temperature to give a reaction mixture. This reaction mixture was recrystallized from a dichloromethane/methyl ethyl ketone mixture to give 14.71 g of 7-deacetyl-6-(4-dimethylaminobutyryl)forskolin. The recrystallization mother liquor was concentrated to give a residue. This residue was recrystallized from diisopropyl ether to further give 9.64 g of 7-deacetyl-6-(4-dimethylaminobutyryl)forskolin (total yield: 84%).

IR(KBr)ν: 3150, 1730, 1710 cm$^{-1}$

EXAMPLE 2-2

7-Deacetyl-6-(4-dimethylaminobutyryl)forskolin 49 mg of 7-deacetyl-7-(4-dimethylaminobutyryl)forskolin was heated to 140° C.

Although its melting point is higher than 140° C., it was molten by heating for a short time.

After one hour, the heating was stopped to give 35 mg of 7-deacetyl-6-(4-dimethylaminobutyryl)forskolin (yield: 71%).

EXAMPLE 2-3

7-Deacetyl-6-(4-dimethylaminobutyryl)forskolin

A mixture comprising 1.00 g of 7-deacetyl-7-(4-dimethylaminobutyryl)forskolin and 15 ml of N,N-dimethylformamide was stirred under heating at 150° C.

After one hour, the reaction was stopped to give 720 mg of 7-deacetyl-6-(4-dimethylaminobutyryrl)forskolin (yield: 72% ).

EXAMPLE 2-4

7-Deacetyl-6-(3-dimethylaminopropionyl)forskolin 40.10 g of 7-deacetyl-7-(3-dimethylaminopropionyl)forskolin was heated to 150° C. and stirred for 10 minutes in a molten state. The reaction mixture was cooled to room temperature and dissolved in 500 ml of dichloromethane. Gaseous dimethylamine was introduced into the solution under cooling with ice. After the completion of the reaction, the reaction mixture was concentrated to give a solid residue. This residue was washed with diisopropyl ether to obtain 19.8 g of 7-deacetyl-6-(3-dimethylaminopropionyl)forskolin (yield: 49%).

The mother liquor after the washing was concentrated to give 23.41 g of a residue. This residue was subjected to the same rearrangement treatment as that described above to further give 9.71 g of 7-deacetyl-6-(3-dimethylaminopropionyl)forskolin (total yield: 74%).

EXAMPLE 2-5

7-Deacetyl-6-piperidinoacetylforskolin 145 mg of 7-deacetyl-7-piperidinoacetylforskolin was heated to 180° C. and allowed to stand for 30 minutes in a molten state. The obtained reaction mixture was cooled and recrystallized from a hexane/ethyl acetate mixture to give 83 mg of 7-deacetyl-6-piperidinoacetylforskolin (yield: 57%).

EXAMPLE 2-6

7-Deacetyl-6-(2,3-dihydroxypropionyl)forskolin 190 mg of a mixture of 7-deacetyl-7-(2,3-dihydroxypropionyl)forskolin diastereoisomers was heated to 210° C. and allowed to stand in a molten state. After 10 minutes, the reaction was stopped to give a mixture of 7-deacetyl-6-(2,3-dihydroxypropionyl)forskolin diastereoisomers.

EXAMPLE 2-7

6-Acetyl-7-deacetylforskolin 120 mg of forskolin was heated to 240° C. and allowed to stand for 5 minutes in a molten state. The reaction mixture was cooled and recrystallized from a hexane/chloroform mixture to give 56 mg of 6-acetyl-7-deacetylforskolin (yield: 47%).

EXAMPLE 2-8

7-Deacetyl-1,6-diacetylforskolin 145 mg of 1-acetylforskolin was heated to 240° C. and allowed to stand in a molten state.

After 5 minutes, the reaction was stopped to give 7-deacetyl-1,6-diacetylforskolin.

EXAMPLE 3-1

7-Deacetyl-6-(3-dimethylaminopropionyl)forskolin 297 mg of 7-deacetyl-7-(3-dimethylaminopropionyl)forskolin, 20 ml of acetonitrile are mixed and refluxed by heating (81.6° C.). After 4 hours, the reaction solution is concentrated under reduced pressure. Obtained residue is diluted with 20 ml of dichloromethane. 2 ml of 50% aqueous dimethylamine solution is added to the solution and stirred for 3 hours at room temperature to obtain 7-deacetyl-6-(3-dimethylaminopropionyl)forskolin.

EXAMPLE 3-2

1.12 g of 7-deacetyl-7-(3-dimethylaminopropionyl)forskolin and 30 ml of acetic acid are mixed and refluxed by heating (118° C.) for 1 hour with stirring to obtain 7-deacetyl-6-(3-dimethylaminopropionyl)forskolin.

EXAMPLE 3-3

1.02 g of 7-deacetyl-7-(3-dimethylaminopropionyl)forskolin and 20 ml of pyridine are mixed and refluxed by heating (115° C.) for 30 hours with stirring to obtain 7-deacetyl-6-(3-dimethylaminopropionyl)forskolin.

EXAMPLE 3-4

394 mg of 7-deacetyl-7-(3-dimethylaminopropionyl)forskolin and 10 ml of 1,1,2,2-tetrachrolethane are mixed and stirred for 22 hours at 130° C. to obtain 7-deacetyl-6-(3-dimethylaminopropionyl)forskolin.

EXAMPLE 3-5

7-Deacetyl-6-(3-dimethylaminopropionyl)-14,15-dihydroforskolin

A mixture of 101 mg of 7-deacetyl-7-(3-dimethylaminopropionyl)-14,15-dihydroforskolin and 10 ml of acetonitrile was heated under reflux for 6 hours. The reaction mixture was cooled, 0.20 ml of 50% of aqueous dimethylamine was added, and stirred for 2.5 hours at room temperature to obtain 7-deacetyl-6-(3-dimethylaminopropionyl)-14,15-dihydroforskolin.

Reference Example 2

7-Deacetyl-7-(3-dimethylaminopropionyl)-14,15-dihydroforskolin hydrochloride

A mixture of 1.00 g of 7-deacetyl-7-(3-dimethylaminopropionyl)forskolin, 26 mg of 5% palladium on carbon catalyst, and 20 ml of methanol was stirred under a hydrogen atmosphere at room temperature for 2 hours to complete the reaction. The reaction mixture was filtered to remove the catalyst. The filtrate was concentrated to obtain an oily residue. This residue was diluted with 5 ml of dichloromethane and 0.6 ml of 4N hydrochloric acid in dioxane was added. The mixture was concentrated and the residue was recrystallized from methanol to obtain 339 mg of 7-deacetyl-7-(3-dimethylaminopropionyl)-14,15-dihydroforskolin hydrochloride (yield: 31%).

m.p. 260°–261° C. (decomp.)

IR(Nujol)ν: 3230, 2720, 1735, 1710 cm$^{-1}$,

MS m/z (relative intensity): 469 ($M^+$ of free base, 6), 159 (11), 118 (41), 116 (12), 86 (16), 84 (25), 71 (11), 69 (11), 58 (100), 57 (16), 55 (16).

What is claimed is:

1. 1,6,7-triacyl-7-deacetylforskolin derivative represented by the general formula:

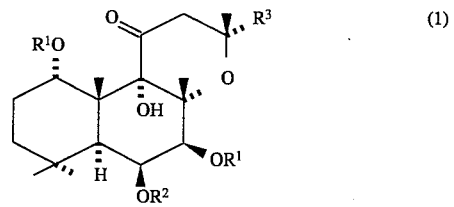

wherein $R^1$ stands for an acyl group, $R^2$ stands for 4-dimethylaminobutyryl, 3-dimethylaminopropionyl, 2-morpholinopropionyl or piperidinoacetyl and $R^3$ stands for an aliphatic group having 2 to 3 carbon atoms or a cyclopropyl group.

* * * * *

UNITED STATES PATENT AND TRADEMARK OFFICE
CERTIFICATE OF CORRECTION

PATENT NO. : 5,610,315
DATED : March 11, 1997
INVENTOR(S) : Tochiro Tatee, Akira Shiozawa, Hirotaka Yamamoto, Yuh-ichiro Ichikawa, Aya Ishikawa, Chikara Komuro, Kazuhisa Narita It is certified that error appears in the above-indentified patent and that said Letters Patent is hereby corrected as shown below:

Title page, item [75],
Inventor Aya Ishikawa should be changed to "Aya Narita."

Signed and Sealed this

Tenth Day of February, 1998

Attest:

BRUCE LEHMAN

Attesting Officer

Commissioner of Patents and Trademarks